(12) United States Patent
Li et al.

(10) Patent No.: US 6,656,200 B2
(45) Date of Patent: Dec. 2, 2003

(54) EMBOLIZATION DEVICE

(75) Inventors: Shu-Tung Li, Oakland, NJ (US); Horng-Ban Lin, Maple Grove, MN (US); Debbie Yuen, Woodcliff Lake, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 56 days.

(21) Appl. No.: 09/827,635

(22) Filed: Apr. 6, 2001

(65) Prior Publication Data

US 2002/0026234 A1 Feb. 28, 2002

Related U.S. Application Data

(60) Provisional application No. 60/196,017, filed on Apr. 7, 2000.

(51) Int. Cl.[7] .............................................. A61M 29/00
(52) U.S. Cl. ....................................... 606/191; 606/198
(58) Field of Search ................................ 606/108, 191, 606/195, 198, 200, 194; 623/11.11

(56) References Cited

U.S. PATENT DOCUMENTS

| 4,994,069 | A |   | 2/1991  | Ritchart et al.  | 606/191 |
|-----------|---|---|---------|------------------|---------|
| 5,354,295 | A |   | 10/1994 | Guglielmi et al. | 606/32  |
| 5,658,308 | A |   | 8/1997  | Snyder           | 606/191 |
| 5,749,894 | A |   | 5/1998  | Engelson         | 606/213 |
| 5,752,974 | A |   | 5/1998  | Rhee et al.      | 606/214 |
| 5,766,160 | A | * | 6/1998  | Samson et al.    | 606/108 |
| 5,833,705 | A | * | 11/1998 | Ken et al.       | 606/191 |
| 5,891,130 | A | * | 4/1999  | Palermo et al.   | 606/1   |
| 5,976,162 | A | * | 11/1999 | Doan et al.      | 606/198 |
| 5,980,550 | A |   | 11/1999 | Eder et al.      | 606/191 |
| 6,254,592 | B1| * | 7/2001  | Samson et al.    | 606/108 |
| 6,280,457 | B1| * | 8/2001  | Wallace et al.   | 606/200 |

* cited by examiner

*Primary Examiner*—Todd E. Manahan
(74) *Attorney, Agent, or Firm*—Fish & Richardson P.C.

(57) ABSTRACT

This invention relates to an embolization device for occluding a vessel. This device includes a matrix made of a biocompatible and biopolymeric material and a radiopaque material, wherein the radiopaque material is interspersed in the biocompatible and biopolymeric material. The matrix can adopt a linear extended form or a folded relaxed form.

25 Claims, 2 Drawing Sheets

100 ——————————————— 11
FIG. 1A
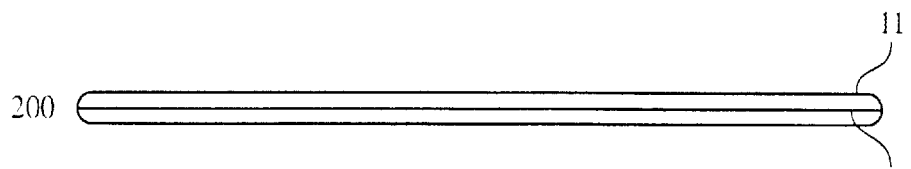
FIG. 1B
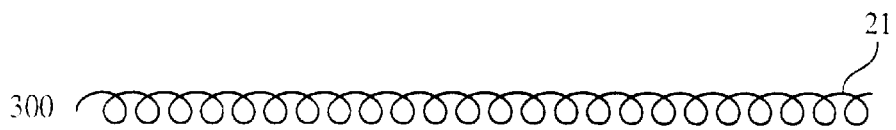
FIG. 1C
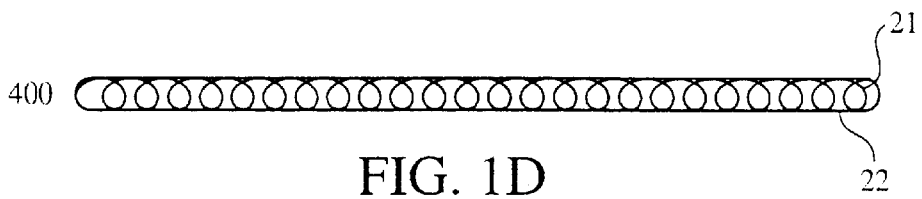
FIG. 1D
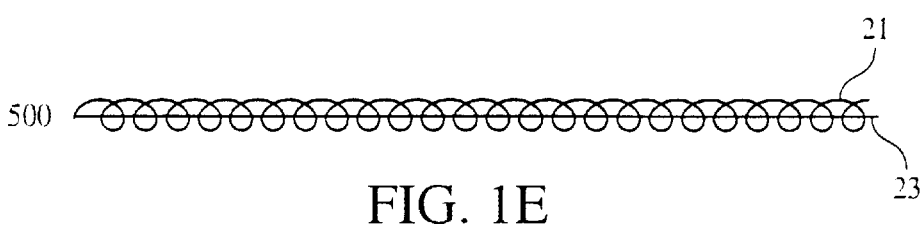
FIG. 1E
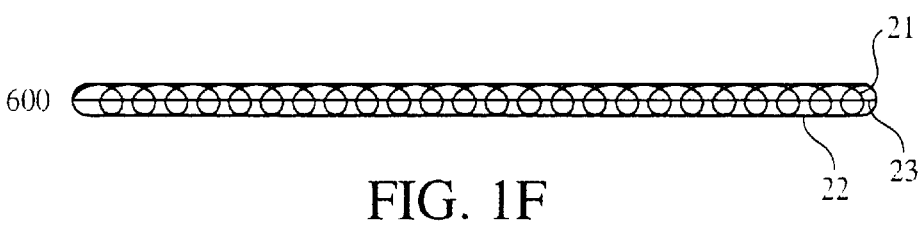
FIG. 1F

EMBOLIZATION DEVICE

CROSS-REFERENCE TO RELATED APPLICATION

Pursuant to 35 U.S.C. §120, this application claims priority to U.S. provisional application No. 60/196,017, filed Apr. 7, 2000, the contents of which are incorporated herein.

BACKGROUND

An embolization device is a surgical implant that is placed within an open site in the vasculature of the human body. The device is typically introduced via a catheter to the open site for endovascular therapy, e.g. control of internal bleeding, occlusion of blood supply to tumors, or relief of vessel wall pressure in the region of an aneurysm. For example, an implantable filament-based device is useful for ligament and tendon repair, vascular repair as an external support of the vascular graft to prevent kinking, and the treatment of aneurysm as an aneurysm sac space filling. See U.S. Pat. No. 5,263,984; Li et al. (1997) *Trans. Soc Bomaterials* 407; and Molyneux et al. (1995) *J. Neurosurg.* 83: 129.

There are a variety of materials that have been used to make such an embolization device. For example, a filament-based device is made of a heavy element such as a heavy metal itself (e.g., iron based stainless steel, nickel-titanium based nitinol, or platinum) or a combination of a heavy element and a polymeric material. It is visible by the X-ray analysis and, therefore, the position of the device can be precisely located and visualized once the device is deployed or implanted in vivo. However, there are many medical applications where a device made of a heavy element itself is not suitable, such as in ligament and tendon repair in which the biomechanical properties of metals are not compatible with the natural ligament and tendon.

SUMMARY

This invention relates to an embolization device for occluding a vessel. This device includes a matrix made of a biocompatible and biopolymeric material and a radiopaque material, wherein the radiopaque material is interspersed in the biocompatible and biopolymeric material. The matrix can further include other agents, e.g., a growth factor, a clotting agent, or a surface active agent. The matrix of this invention can adopt a linear extended form or a folded relaxed form. It can be of mono-filament or multi-filament construction. Preferably, the biocompatible and biopolymeric material is biodegradable.

In one aspect, the embolization device of this invention includes a matrix that adopts a linear extended form or a folded relaxed form. One linear extended form the matrix may adopt is non-coiled, which can fold into a relaxed form, such as a spherical, a random, or a cylindrically coiled form. Another linear extended form the matrix may adopt is coiled, which can fold into a relaxed form as well, such as a spherical, a random, or a cylindrically coiled form. The coiled extended matrix defines a channel, in which a strand can be further disposed. The strand may be made of a biocompatible and biopolymeric material and adopt the linear extended form or the folded relaxed form as part of the matrix. It can be mono-filament or multi-filament construction. Preferably, the strand is made of a biocompatible and biopolymeric material that is biodegradable. Optionally, the strand is made of a biocompatible and biopolymeric material in which a radiopaque material is interspersed.

In another aspect, the embolization device of this invention can include a matrix and a sheath surrounding the matrix, wherein the sheath is made of a biocompatible and biopolymeric material. The sheath can further include other agents, e.g., a growth factor, a clotting agent, or a surface-active agent. As above described, the matrix can adopt a linear extended form, such as a non-coiled form, a coiled form, or a coil defining a channel in which a strand can be further disposed, and the sheath may adopt a linear extended form as well. The embolization device including the matrix and the sheath can adopt a folded relaxed form, such as a spherical, a random, or a cylindrically coiled form. Preferably, the sheath is made of a biocompatible and biopolymeric material that is biodegradable. Optionally, the sheath is made of a biocompatible and biopolymeric material in which a radiopaque material is interspersed.

In a further aspect, the embolization device of this invention can include a matrix, or a matrix and a sheath. The biocompatible and biopolymeric material used for this device can be a collagen (e.g., type I to type XIV collagens). As above described, the matrix can adopt a linear extended form, such as a non-coiled form, a coiled form, or a coil defining a channel in which a strand can be further disposed, as well as the sheath, if present, which is also in its linear extended form. The embolization device including the matrix and the sheath, if present, can adopt a folded relaxed form, such as a spherical, a random, or a cylindrically coiled form. Optionally, the sheath is made of collagen in which a radiopaque material is interspersed.

Also within the scope of this invention is a method of preparing an embolization device for occluding a vessel. The method includes steps of preparing a dispersion or a solution of a mixture of a biocompatible and biopolymeric material and a radiopaque material; reconstituting the mixture from the dispersion or the solution to form a filament; fabricating a matrix suitable for endovascular therapy, for example, with the filament or multiple filaments; crosslinking the matrix; and drying the matrix. Alternatively, the method includes steps of fabricating a matrix and a sheath suitable for endovascular therapy, for example, with the filament or multiple filaments; crosslinking the matrix and the sheath; and drying the matrix and the sheath. The matrix and sheath may be coated with a lubricious agent, e.g., a hyaluronic acid, to facilitate the delivery.

The details of this invention are set forth in the accompanying drawings and the description below. Other features, objects, and advantages of the invention will be apparent from the description and drawings, and from the claims.

DESCRIPTION OF DRAWINGS

In the drawings, which are not to scale:

FIGS. 1A–1F are schematic views illustrating the linear extended forms that the embolization device of this invention may adopt. The device can include a matrix that is in the extended form of a non-coiled form (1A), a coiled form (1C), or a coil defining a channel in which a strand can be disposed (1E). The device can include a matrix and a sheath that adopts a linear extended form as the matrix, wherein the matrix can be in the extended form of a non-coiled form (1B), a coiled form (1D), or a coil defining a channel in which a strand can be disposed (1F).

Like reference symbols in the various drawings indicate like elements.

DETAILED DESCRIPTION

Materials

Figure 2A:
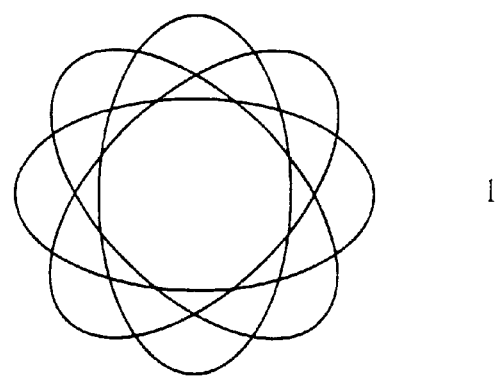
FIGS. 2A–2C are schematic views illustrating the folded relaxed forms that the embolization device of this invention may adopt. The relaxed form can be a spherical (2A), a random (2B), or a cylindrically coiled (2C) form.

The term "biocompatible and biopolymeric" refers to a polymer having of a series of subunits of an appropriate type, e.g., an amino acid, which is compatible with human tissues. The biocompatible and biopolymeric material can exhibit effects in vivo, such as thrombogenicity or the like. Thrombogenicity is used to refer to any substance that increases or promotes adhesion of any of the components of blood or plasma, including but not limited to, blood cells, platelets, and other blood-borne components that would lead to the clot formation of the blood. The biocompatible and biopolymeric material can be a protein (e.g., collagen, gelatin, fibrin, or silk) or a polysaccaride (e.g., hyaluronic acid, or alginic acid). In one aspect of this invention, the biocompatible and biopolymeric material is a collagen. In particular, the collagen, e.g., type I collagen, can be isolated from human or animal tissues, such as tendon, skin, bone, or ligament. See, for example, Miller and Rhodes, (1982) *Methods in Enzymology* 82: 33–64. It can be further purified by a method of retaining a terminal peptide, i.e., a telopeptide (see, for example, U.S. Pat. No. 3,114,593), or alternatively, by a method of removing the telopeptide (see, for example, U.S. Pat. No. 4,233,360). The collagen can also be genetically engineered (e.g., collagen marketed by Fibrogen, Inc., Palo Alto, Calif.) or be synthesized by fibroblasts in vitro (e.g., collagen prepared by Advanced Tissue Sciences, La Jolla, Calif.). The purified collagen can be cross-linked either by chemical reagents or by other means such as UV light. Reagents useful as cross-linking agents include those described in, for example, U.S. Pat. No. 6,177,514. Preferably, the collagen is cross-linked chemically by such reagents as glutaraldehyde, formaldehyde, acrolein, or chromium salts.

The term "radiopaque" refers to a non-toxic material capable of being monitored or detected during injection into a mammalian subject by, for example, radiography or fluoroscopy. The radiopaque material can be either water soluble or water insoluble. Examples of water soluble radiopaque materials include metrizamide, iopamidol, iothalamate sodium, iodomide sodium, and meglumine. Examples of water insoluble radiopaque materials include tantalum, tantalum oxide, and barium sulfate, which are commercially available in the proper form for in vivo use. Other water insoluble radiopaque materials include, but are not limited to, gold, tungsten, stainless steel, and platinum.

Materials useful for making the embolization device of this invention include a biocompatible and biopolymeric material and a radiopaque material, wherein the radiopaque material is interspersed in the biocompatible and biopolymeric material. Such a material can be prepared by mixing the biocompatible and biopolymeric material and the radiopaque material. For example, a collagen-based material can be prepared by adding a sufficient amount of collagen to a solvent, which can be an aqueous solution, e.g., lactic acid solution. When the collagen is not soluble, homogenization can be used to form a collagen dispersion. The amount of collagen in a dispersion or in a solution can be in the range of 0.3 to 5.0% by weight, preferably, 0.5 to 2.0% by weight. A filtration can be further performed to remove any large size particles. Then, a sufficient amount of a radiopaque material can be added to the dispersion or the solution. In general, a collagen-based material may include the radiopaque material in the range of 10 to 90% by weight, preferably, 30 to 80% by weight. When the radiopaque material is not soluble, a means such as stirring, homogenization, or sonicating may be employed. The obtained collagen-based material can be used to prepare a filament of this invention.

In addition, one or more active agents selected from the group consisting of growth factors, clotting agents, surface active agents, and tissue attachment factors (e.g., fibronectin or laminin) may be added to the above-described material to facilitate an occlusion of a blood vessel or to deliver the active reagents into a blood vessel locally. Alternatively, the active agent can be added by coating onto the embolization device of this invention. A lubricating agent such as the hyaluronic acid or the like can be used to coat the device to facilitate the delivery of the device through the micro-catheter.

Devices

The device of this invention can be introduced to a site for endovascular therapy through a catheter in its linear extended form (FIGS. 1A–1F) and wherein it may adopt its folded relaxed form (FIGS. 2A–2C) upon released or upon delivered to the occlusion site from the end of the catheter. Each linear extended form will fold into one of the relaxed forms depending on how the embolization device is fabricated.

FIG. 1A shows an embolization device in its linear extended form (100). The device contains a non-coiled matrix (11), which can be formed of mono-filament or multi-filament construction. The matrix (11) can be of a diameter suitable for endovascular therapy, for example, in the range of 0.004 to 0.100 inch (0.101 to 2.54 mm), preferably in the range of 0.008 to 0.500 inch (0.202 to 1.27 mm).

FIG. 11B shows an embolization device in its linear extended form (200). The device is encased non-coiled, which includes a matrix (11) and a sheath (12) surrounding the matrix (11). The term "surrounding" refers to substantially surrounding wherein the most part of the matrix is covered by the sheath. The sheath (12) is in its linear extended form as the matrix (11), and can fold into its relaxed form as the matrix (11) folds. The sheath (12) can be a tube with a wall of thickness suitable for endovascular therapy, for example, in the range of 0.0008 to 0.02 inch (0.02 to 0.5 mm). The sheath (12) can be made of a biocompatible and biopolymeric material, preferably, a biodegradable biocompatible and biopolymeric material. The incorporation of the sheath can significantly improve the rigidity of the matrix, which favors delivering the device to a site in an artery through a micro-catheter.

FIG. 1C shows an embolization device in its linear extended form (300). The device contains a coiled matrix (21). The coil (21) can be formed of a plurality of windings that are axially spaced (i.e., a pitch of the windings). Although the device shown in this figure has a circular cross-section, it could have other cross-sectional shapes, e.g., rectangular, oval, square, or triangular. The matrix (21) can be of a diameter suitable for endovascular therapy, for example, in the range of 0.004 to 0.100 inch (0.101 to 2.54 mm). The coil may have a winding pitch suitable for endovascular therapy, for example, in the range of 0.0 to 0.10 inch (0 to 2.54 mm), preferably in the range of 0.004 to 0.05 inch (0.1 to 1.27 mm), wherein the winding pitch can be uniform or nonuniform along the length of the coil.

FIG. 1D shows an embolization device in its linear extended form (400). The device is encased coiled, which includes a matrix (21) and a sheath (22) surrounding the matrix (21).

FIG. 1E shows an embolization device in its linear extended form (500). The device contains a coiled matrix (21), in which a central channel is open. A strand (23), formed of mono-filament or multi-filaments, extends axially through the open channel. The size of the strand (23) may depend upon the inner diameter of the coil. The strand (23), as part of the matrix, can be made of a biocompatible and biopolymeric material, preferably, a biodegradable biocompatible and biopolymeric material. A strand can provide a large thrombogenic surface area, via swelling of the matrix, which allows for increased tissue growth, which can facilitate an occlusion of a blood vessel.

FIG. 1F shows an embolization device in its linear extended form (600). The device is an encased coiled, which contains a matrix (21) with a strand (23), and a sheath (22) surrounding the matrix (21).

FIG. 2A depicts an embolization device in its spherical relaxed form (1). The spherical form (1) is formed of regularities in a plurality of turns. The regularities offset the helical axis of each turn, resulting in a globular shape device having a diameter suitable for endovascular therapy, for example, in the range of 0.039 to 0.78 inch (1 to 20 mm), preferably in the range of 0.118 to 0.39 inch (3 to 10 mm).

Figure 2B:
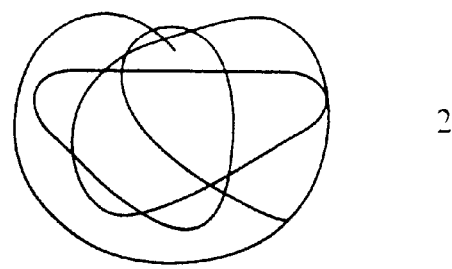

FIG. 2B depicts an embolization device in its random relaxed form (2). This randomly shaped device (2) can form substantially a space-filling mass when it is released into a site of an artery.

Figure 2C:
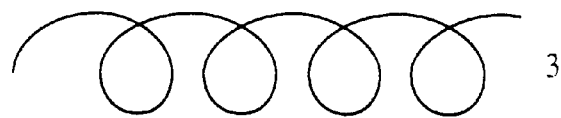

FIG. 2C depicts an embolization device in its cylindrically coiled relaxed form (3). This device (3) is formed of an elongated cylindrical coil having a plurality of windings that are axially spaced, either uniformly or nonuniformly, having a diameter suitable for endovascular therapy, for example, in the range of 0.039 to 0.78 inch (1 to 20 mm) in diameter and 0.078 to 0.78 inch (2 to 20 mm) in length, preferably in the range of 0.118 to 0.39 inch (3 to 10 mm) in diameter and 0.160 to 0.39 inch (4 to 10 mm) in length.

Each of the linear extended forms may fold into one of the relaxed forms. For example, an embolization device (303) can adopt a linear extended form (300) or a cylindrically coiled relaxed form (3). In another example, an embolization device (401) can adopt an encased coiled extended form (400) or a spherical relaxed form (1). Another embolization device (103) can adopt a non-coiled extended form (100) or a cylindrically coiled relaxed form (3).

In addition to the coils shown in the figures, the embolization device may be formed of alternate configurations, for example, woven braids rather than the coils. In another example, small size filaments may be attached to the windings of a coil, such as a device (300), by tying or with adhesives. It is also within the scope of this invention that the embolization device can have shapes or structures other than coils or braids, for example, solid sphere structures or the like.

Fabrication

The most basic element for fabricating the embolization device of this invention is a filament. Multiple filaments may be used for a matrix, and/or a strand. Each filament can be made using a conventional method. For example, a collagen-based filament can be made by a method described in Li, et al., U.S. Pat. No. 5,263,984, Schimpf and Rodriguez (1977) *Ind. Eng. Chem., Prod. Res. Dev.* 16: 90–92, Kito and Silver (1990) *Biomaterials* 11: 169–175, or U.S. Pat. No. 3,114, 593. More specifically, a dispersion or a solution containing a collagen-based material can be filled in a syringe, which is loaded onto a programmable syringe pump. The dispersion or the solution is extruded, and the extruded filament is dehydrated in a solvent such as an alcohol and then dried in air or by freeze drying.

The embolization device of this invention may be made using conventional equipment and procedures. For example, an embolization device (303) can be fabricated by using a matrix (11) containing one filament or multiple filaments. The fabrication includes processing steps of:

(1) winding the matrix (11) onto a plastic or metal wire with a desired winding pitch to form a coil (21);

(2) winding the coil (21) onto a plastic or metal mandrel for a plurality turns to form an embolization device (303);

(3) crosslinking the embolization device (303) in a solution containing one or more crosslinking reagents;

(4) removing the residual crosslinking reagent from the embolization device (303) by rinsing in distilled water or a phosphate buffer;

(5) drying the embolization device (303) in air or by freeze drying; and (6) removing the embolization device (303) from the mandrel, then from the wire.

In another example, an embolization device (401) can be fabricated by using a matrix (11) containing one filament or multiple filaments. The fabrication includes processing steps of:

(1) winding the matrix (11) onto a plastic or metal wire with a desired winding pitch to a coil (21);

(2) using the coil (11) as a mandrel, which is slowly rotating;

(3) coating the coil (11) with a solution containing a biocompatible and biopolymeric material to form a sheath (22), and thus forming an encased coil (400);

(4) winding the encased coil (400) onto a plastic or metal ball-shaped mandrel for a plurality turns to form an embolization device (401);

(5) crosslinking the embolization device (401) in a solution containing one or more crosslinking reagents;

(6) removing the residual crosslinking reagent from the embolization device (401) by rinsing in distilled water or a phosphate buffer;

(7) drying the embolization device (401) in air or by freeze drying; and (8) removing the embolization device (401) from the mandrel, then from the wire.

Other manners for fabricating the embolization device of this invention may include placing a strand (23), which is formed of mono-filament or multi-filaments, in the central channel of a coil (21) prior to the crosslinking step. If a multiplicity of filaments is employed, their ends may or may not be bound. The binding can be performed by heat, adhesives, or mechanical means.

Embolization

The term "embolization" refers to a process wherein a device is brought to a site of an artery, and the process will fill or plug the vessel and encourages clot formation so that blood flow in the vessel ceases.

The embolization device of this invention may be placed within vessels using procedures well known in the art. See, for example, U.S. Pat. Nos. 4,994,069 and 5,304,194. Normally, a catheter is advanced, using state-of-the-art vascular intervention techniques, to a site of an artery where an occlusion is desired. The embolization device can be transferred to the lumen of the catheter by a pusher rod. The pusher rod can exert a force on the proximal end of the embolization device and push it through the catheter lumen to the distal end of the catheter. The location of the embolization device may be visualized by any suitable detection method, such as X-ray. Once at the desired release site, the embolization device can be pushed from the catheter lumen into the blood vessel. In the catheter, the embolization device adopts a linear extended form such as those illustrated in FIGS. 1A to 1F. Upon release from the catheter, the embolization device adopts a folded relaxed form such as those illustrated in FIGS. 2A to 2C. Typically, one or more embolization devices of this invention are delivered to the site of an artery. Those devices may or may not adopt the same linear extended forms or the same folded relaxed forms. When placed in a vasculature, one or more embolization devices consisting of a biocompatible and biopolymeric material will promote thrombosis, facilitate fibrotic tissue deposition, and hasten occlusion of the vasculature.

In addition to the method described above, an embolization device may be attached to the distal end of a catheter via a cleavable joint (e.g., a joint that is cleavable by heat, electrolysis, or other means), or a mechanical joint, which permits the device to be detached. Electrolytical joints are exemplified in U.S. Pat. Nos. 5,122,136; 5,134,295; 5,423,829; 5,522,836; and 5,624,449. A heat-cleavable joint is exemplified in U.S. Pat. No. 5,108,407. Mechanical joints are exemplified in U.S. Pat. Nos. 5,234,437; 5,250,071; 5,261,916; and 5,350,397.

The specific materials, methods, and examples herein are to be construed as merely illustrative, and not limitative of the disclosure in any way whatsoever. Without further elaboration, it is believed that one skilled in the art can, based on the description herein, utilize the present invention to its fullest extent. All publications, patents, and other references cited herein are hereby incorporated by reference in their entirety.

EXAMPLE 1

A Method for Preparing a Collagen-based Embolization Device (103)

Purified bovine type I collagen is suspended in 0.07 M lactic acid solution to form a 0.7% (w/v) collagen dispersion. The collagen dispersion is homogenized in a Silverson homogenizer for 60 seconds. The homogenized dispersion is filtered through a 100 mesh stainless steel filter to remove large size particles. High purity tantalum powder (>99.8% purity, 5–10 mm in size) is added into the collagen dispersion and stirred. The dispersion is degased under vacuum ($100$–$300 \times 10^{-6}$ torr), then transferred to a 30 c.c. syringe.

The syringe is loaded onto a programmable syringe pump. The tip of the syringe is connected to a 16 guage blunt-tipped needle, a three-way connector, and a coacervation tubing. The flow of the coacervation solution (0.3% $NH_4OH$) is controlled by a laboratory pump. Collagen dispersion is extruded into the coacervation solution at a rate of approximately 2.0 ml/min. Extruded collagen filaments are dehydrated in isopropanol and dried in air.

The collagen filaments is wound onto a Teflon® coated mandrel and crosslinked in a solution containing 0.05% glutaraldehyde to form a coil. The coil is thoroughly rinsed in distilled water to remove glutaraldehyde residues and dried in air. The thus obtained embolization device (103), containing 50–80% by weight tantalum, is 6 mm in diameter and 15 cm in length.

EXAMPLE 2

A Method for Using Embolization Device to Occlude Aneurysms

Arterial aneurysms are created in New Zealand White rabbits (4–5 kg) using a technique described by Kallmes et al. (1999) *Radiology* 213: 217–222. Animal anesthesia is induced with an intramuscular injection of ketamine (60 mg/kg) and xylazine (6 mg/kg). Using standard sterile techniques, the right common femoral artery of the rabit is surgically exposed. The artery is ligated distally using surgical sutures and a 22 gauge arterial catherter is advanced retrograde into the artery. A 0.0018" guidewire is passed through the catheter, and serial dilations are performed to place a 5 French vascular sheath. A collagen-based embolization device containing 80% tantalum is prepared according to the method of EXAMPLE 1. The device is 6 mm in diameter and 15 cm in length. It is held in place by a 3 French Biotome catheter® (Cook Inc., Bloomington, Ind.) and is loaded at the tip of a 5 French catheter. Under a fluoroscope guidance, the tip of the catheter is advanced into the aneurysm cavity, then the collagen-based device is deployed within the aneurysm cavity. After the device is deployed, follow-up anigography is performed. Near-complete occlusion is immediately achieved. Two weeks following deployment of the device, angiography shows the treated aneurysm remains occluded.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An embolization device, comprising a matrix that includes a biodegradable and biocompatible biopolymeric material and a radiopaque material, wherein the radiopaque material is interspersed in the biopolymeric material, and the matrix adopts a linear extended form or a folded relaxed form.

2. The embolization device of claim 1, wherein the extended form is non-coiled.

3. The embolization device of claim 2, wherein the relaxed form is spherical, random, or cylindrically coiled.

4. The embolization device of claim 1, wherein the extended form is a coil defining a channel.

5. The embolization device of claim 4, further comprising a strand disposed in the channel, wherein the strand includes a biocompatible and biopolymeric material and adopts a linear extended form or a folded relaxed form as part of the matrix.

6. The embolization device of claim 5, wherein the relaxed form is spherical, random, or cylindrically coiled.

7. The embolization device of claim 4, wherein the relaxed form is spherical, random, or cylindrically coiled.

8. The embolization device of claim 1, further comprising a sheath surrounding the matrix, wherein the sheath includes a biocompatible and biopolymeric material and adopts a linear extended form or a folded relaxed form as the matrix.

9. The embolization device of claim 8, wherein the extended form is non-coiled.

10. The embolization device of claim 9, wherein the relaxed form is spherical, random, or cylindrically coiled.

11. The embolization device of claim 8, further comprising a strand disposed in the channel, wherein the strand includes a biocompatible and biopolymeric material and adopts a linear extended form or a folded relaxed form as part of the matrix.

12. The embolization device of claim 11, wherein the relaxed form is spherical, random, or cylindrically coiled.

13. The embolization device of claim 8, wherein the extended form is a coil defining a channel.

14. The embolization device of claim 13, wherein the relaxed form is spherical, random, or cylindrically coiled.

15. The embolization device of claim 1, wherein the biocompatible and biopolymeric material is a collagen.

16. The embolization device of claim 15, wherein the extended form is non-coiled.

17. The embolization device of claim 16, wherein the relaxed form is spherical, random, or cylindrically coiled.

18. The embolization device of claim 15, wherein the extended form is a coil defining a channel.

19. The embolization device of claim 18, further comprising a strand disposed in the channel, wherein the strand includes a biocompatible and biopolymeric material and adopts a linear extended form or a folded relaxed form as part of the matrix.

20. The embolization device of claim 19, wherein the relaxed form is spherical, random, or cylindrically coiled.

21. The embolization device of claim 18, wherein the relaxed form is spherical, random, or cylindrically coiled.

22. The embolization device of claim 15, further comprising a sheath surrounding the matrix, wherein the sheath includes a biocompatible and biopolymeric material and adopts a linear extended form or a folded relaxed form as the matrix.

23. The embolization device of claim 22, wherein the extended form is non-coiled.

24. The embolization device of claim 22, wherein the extended form is a coil defining a channel.

25. The embolization device of claim 22, further comprising a strand disposed in the channel, wherein the strand includes a biocompatible and biopolymeric material and adopts a linear extended form or a folded relaxed form as part of the matrix.

* * * * *